United States Patent
Hamauzu

(10) Patent No.: US 9,788,806 B2
(45) Date of Patent: Oct. 17, 2017

(54) NOISE REDUCTION DEVICE, METHOD AND PROGRAM

(71) Applicant: FUJIFILM Corporation, Tokyo (JP)

(72) Inventor: Shin Hamauzu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 49 days.

(21) Appl. No.: 15/063,683

(22) Filed: Mar. 8, 2016

(65) Prior Publication Data
US 2016/0292851 A1 Oct. 6, 2016

(30) Foreign Application Priority Data
Mar. 31, 2015 (JP) .................. 2015-073305

(51) Int. Cl.
| | |
|---|---|
| G06T 7/00 | (2017.01) |
| A61B 6/00 | (2006.01) |
| G06K 9/52 | (2006.01) |
| G06T 5/00 | (2006.01) |

(52) U.S. Cl.
CPC ............ *A61B 6/502* (2013.01); *A61B 6/5258* (2013.01); *G06T 5/002* (2013.01); *G06T 2207/10116* (2013.01); *G06T 2207/20012* (2013.01); *G06T 2207/30068* (2013.01)

(58) Field of Classification Search
CPC ....... A61B 6/502; A61B 6/5258; G06T 5/002; G06T 2207/10116; G06T 2207/20012; G06T 2207/30068
See application file for complete search history.

(56) References Cited

U.S. PATENT DOCUMENTS

| | | | | |
|---|---|---|---|---|
| 2010/0246924 A1* | 9/2010 | Morita | ............... | A61B 5/4872 382/132 |
| 2011/0229006 A1* | 9/2011 | Morita | ............... | G06T 7/0012 382/132 |
| 2015/0363904 A1* | 12/2015 | Arai | ................. | G06T 5/003 382/131 |

FOREIGN PATENT DOCUMENTS

JP 2005-021456 A 1/2005

OTHER PUBLICATIONS

Zhang et al. "The Application of Adaptive Enhancement Algorithm Based on Gray Entropy in Mammary Gland CR Image." 2nd International Conference on Consumer Electronics, Communications and Network, Apr. 21, 2012, pp. 2937-2940.*

(Continued)

*Primary Examiner* — Jon Chang
(74) *Attorney, Agent, or Firm* — Sughrue Mion, PLLC

(57) ABSTRACT

A breast composition information acquisition section acquires a mammary gland content ratio in each unit pixel in a breast region of a radiological image obtained by irradiating a breast of a subject with radiation. A noise reduction section acquires an index value indicating the size of a variance range of pixel values at each unit pixel position from the mammary gland content ratio of each unit pixel, performs a noise reduction process so that the level of noise reduction at a position of an attention pixel is low as the index value is small, and performs the noise reduction process so that the level of noise reduction at the position of the attention pixel is high as the index value is large.

20 Claims, 6 Drawing Sheets

(56) References Cited

OTHER PUBLICATIONS

Sakellaropoulos et al. "An Adaptive Wavelet-Based Method for Mammographic Image Enhancement." 14th International Conference on Digital Signal Processing, Jul. 1, 2002, pp. 453-456.*
Ali et al. "Enhancement and GIF Filtering for the Improvement of the Mammographique Image." First International Symposium on Control, Communications and Signal Processing, Mar. 21, 2004, pp. 247-250.*

* cited by examiner

NOISE REDUCTION DEVICE, METHOD AND PROGRAM

CROSS-REFERENCE TO RELATED APPLICATIONS

The present application claims priority under 35 U.S.C. §119 to Japanese Patent Application No. 2015-073305, filed on Mar. 31, 2015. The above application(s) is hereby expressly incorporated by reference, in its entirety, into the present application.

BACKGROUND OF THE INVENTION

1. Field of the Invention

The present invention relates to a noise reduction device, a noise reduction method, and a non-transitory computer readable recording medium storing a noise reduction program that perform a noise reduction process for removing quantum noise included in a radiological image obtained by image-capturing a breast according to the amount of mammary glands included in the breast.

2. Description of the Related Art

In the related art, when performing diagnosis using a radiological image of a subject, a technique of performing image processing such as a frequency emphasis process and a gradation process with respect to a radiological image obtained by image capturing to acquire an image suitable for diagnosis and displaying the image on a display device such as a liquid crystal monitor or outputting the image as a hard-copy on a film has been used. Here, the radiological image has a problem in that quantum noise of radiation is conspicuous in a portion where the dose of radiation is small and the density is low. Thus, various methods of performing a noise reduction process for reducing or removing the quantum noise included in the radiological image as image processing with respect to the radiological image have been proposed.

As the noise reduction process, a smoothing process using a smoothing filter corresponding to quantum noise is known. For example, JP2005-021456A discloses a technique that determines the level of noise reduction using information indicating whether a portion where the degree of concentration of a density gradient vector that appears on a radiological image corresponds to a location where there is a high probability that an image of a tumor or the like is present or a location where there is a high probability that the image is noise and information indicating the dose of radiation that reaches the radiological image.

SUMMARY OF THE INVENTION

In the related art, noise reduction is controlled based on radiation dose information, and if the dose of radiation is small, it is considered that the amount of noise is large. Then, the noise reduction is strengthened. Further, in JP2005-021456A, the level of noise reduction varies between a location where an image of a tumor or the like is present and a location where noise is present.

However, in a case where the dose of passed radiation is the same between a fatty beast image and a high density breast image, if the same level of noise reduction is performed, in the high density breast image, mammary gland information becomes crushed and blurred. Although it is necessary to leave a thin structure such as a mammary gland, if the level of noise reduction is increased to reduce noise because of a large amount of noise in the high density region, the mammary gland information breaks down.

In order to solve the above problems, an object of the invention is to provide a noise reduction device, a noise reduction method, and a non-transitory computer readable recording medium storing a noise reduction program capable of performing noise reduction without crushing thin shading such as mammary glands that appear on a radiological image obtained by image-capturing a breast.

According to an aspect of the invention, there is provided a noise reduction device including: a breast composition information acquisition section that irradiates a breast of a subject with radiation and acquires a mammary gland content ratio in each unit pixel including a predetermined number of pixels that form a breast region of a radiological image obtained by the radiation that passes through the breast; and a noise reduction section that sets, using each unit pixel as an attention pixel, an interest region including the attention pixel, acquires an index value indicating a size of a change of the mammary gland content ratio of each unit pixel that is present in the interest region from the mammary gland content ratios of the plurality of unit pixels that is present in the interest region, performs a noise reduction process so that the level of noise reduction at a position of the attention pixel is low as the index value is small, and performs the noise reduction process so that the level of noise reduction at the position of the attention pixel is high as the index value is large.

According to another aspect of the invention, there is provided a noise reduction method in a noise reduction device including a breast composition information acquisition section and a noise reduction section, the method including: a breast composition information acquisition step of irradiating a breast of a subject with radiation and acquiring a mammary gland content ratio in each unit pixel including a predetermined number of pixels that form a breast region of a radiological image obtained by the radiation that passes through the breast, by the breast composition information acquisition section; and a noise reduction step of setting, using each unit pixel as an attention pixel, an interest region including the attention pixel, acquiring an index value indicating a size of a change of the mammary gland content ratio of each unit pixel that is present in the interest region from the mammary gland content ratios of the plurality of unit pixels that is present in the interest region, performing a noise reduction process so that the level of noise reduction at a position of the attention pixel is low as the index value is small, and performing the noise reduction process so that the level of noise reduction at the position of the attention pixel is high as the index value is large, by the noise reduction section.

According to still another aspect of the invention, there is provided a non-transitory computer readable recording medium storing a noise reduction program that causes a computer to function as: a breast composition information acquisition section that irradiates a breast of a subject with radiation and acquires a mammary gland content ratio in each unit pixel including a predetermined number of pixels that form a breast region of a radiological image obtained by the radiation that passes through the breast; and a noise reduction section that sets, using each unit pixel as an attention pixel, an interest region including the attention pixel, acquires an index value indicating a size of a change of the mammary gland content ratio of each unit pixel that is present in the interest region from the mammary gland content ratios of the plurality of unit pixels that is present in the interest region, performs a noise reduction process so that the level of noise reduction at a position of the attention pixel is low as the index value is small, and performs the noise reduction process so that the level of noise reduction at the position of the attention pixel is high as the index value is large.

The "unit pixel including a predetermined number of pixels" may be a single pixel or may be a group of plural pixels that are adjacent to each other, which refers to a predetermined number of pixels capable of being considered as a single unit. Specifically, for example, two pixels, four pixels, or the like, that are adjacent to each other are set as the unit pixel. Alternatively, a group of plural pixels that are close to each other may be set as the pixel unit. These close pixels refer to pixels that are included in a range of a predetermined shape such as a circle or a rectangle with a predetermined size, and include all pixels in the range. The number of pixels that form the unit pixel may be determined according to a resolution or an S value (reading sensitivity) of an image. With respect to the S value, refer to JP 1990-108175A (JP-H02-108175A) or the like.

The "interest region" refers to a region having a predetermined size and a predetermined shape in which an attention pixel is present at approximately the center thereof in the case where each unit pixel on a radiological image is set as the attention pixel. The shape may be a rectangle, a circle or other shapes, but a size suitable for determining whether each unit pixel on the radiological image is at a place where there is a large amount of mammary glands or at a place where there is a small amount of mammary glands from pixel values of the unit pixels that are present in the interest region may be empirically determined. Further, it is preferable that the attention pixel is present in the vicinity of the center of the interest region, but this is not essential.

The "index value indicating the size of the change of the mammary gland content ratio of the unit pixel that is present in the interest region" refers to an index value indicating the size of the change of the mammary gland content ratio, calculated from the radiation that passes through mammary gland tissue and adipose tissue in the interest region, and represents the size of the change of the mammary gland content ratio that is not affected by noise and structures other than mammary glands. Specifically, for example, the index value may be a maximum value and a minimum value of the mammary gland content ratios of respective unit pixels in the interest region, or a statistical variance of the mammary gland content ratios of the respective unit pixels that are present in the interest region.

Further, the noise reduction section may calculate the index value so that the index value is small as a representative value of the mammary gland content ratios of the plural unit pixels that are present in the interest region is large and is large as the representative value of the mammary gland content ratios is small.

The "representative value" refers to a value that represents the mammary gland content ratios of the plural unit pixels in the interest region, and specifically, may be a median value, an average value, a modal value, or the like. The "median value" refers to a value disposed at the center in the case where the mammary gland content ratios are arranged in an ascending order. The "average value" refers to a value obtained by averaging the mammary gland content ratios that appear in the interest region. The "modal value" refers to a value that most frequently appears among the mammary gland content ratios that appear in the interest region.

Further, the breast composition information acquisition section may acquire the mammary gland content ratio in each unit pixel according to the dose of the radiation applied to the breast, a pixel value of each unit pixel of the radiological image, and the thickness of the breast.

Further, the breast composition information acquisition section may acquire the mammary gland content ratio in each unit pixel using a pixel value of a location which is estimated to be formed by only adipose tissue in the breast region of the radiological image and a pixel value of each unit pixel in the breast region.

Furthermore, the unit pixel may be a single pixel.

According to still another aspect of the invention, there is provided a noise reduction device including: a breast composition information acquisition section that irradiates a breast of a subject with radiation and acquires a mammary gland content ratio at which mammary glands are included in the breast from a radiological image obtained by the radiation that passes through the breast; and a noise reduction section that performs a noise reduction process so that the level of noise reduction with respect to the radiological image is low as the mammary gland content ratio is high, and performs the noise reduction process so that the level of noise reduction with respect to the radiological image is high as the mammary gland content ratio is low.

According to still another aspect of the invention, there is provided a noise reduction method in a noise reduction device including a breast composition information acquisition section and a noise reduction section, the method including: a breast composition information acquisition step of irradiating a breast of a subject with radiation and acquiring a mammary gland content ratio at which mammary glands are included in the breast from a radiological image obtained by the radiation that passes through the breast, by the breast composition information acquisition section; and a noise reduction step of performing a noise reduction process so that the level of noise reduction with respect to the radiological image is low as the mammary gland content ratio is high, and performing the noise reduction process so that the level of noise reduction with respect to the radiological image is high as the mammary gland content ratio is low, by the noise reduction section.

According to still another aspect of the invention, there is provided a non-transitory computer readable recording medium storing a noise reduction program that causes a computer to function as: a breast composition information acquisition section that irradiates a breast of a subject with radiation and acquires a mammary gland content ratio at which mammary glands are included in the breast from a radiological image obtained by the radiation that passes through the breast; and a noise reduction section that performs a noise reduction process so that the level of noise reduction with respect to the radiological image is low as the mammary gland content ratio is high, and performs the noise reduction process so that the level of noise reduction with respect to the radiological image is high as the mammary gland content ratio is low.

Further, the breast composition information acquisition section may calculate the mammary gland content ratio from a ratio between the area of a breast region on the radiological image and the area of a mammary gland region on the radiological image.

In addition, it is preferable that the noise reduction device further includes: a noise amount estimation section that estimates the amount of noise according to information indicating the dose of radiation which is applied to the breast and reaches the radiological image and the noise reduction section increases the level of noise reduction as the estimated amount of noise is large and decreases the level of noise reduction as the estimated amount of noise is small.

Furthermore, the noise reduction section may perform the noise reduction process using a smoothing filter, and may decrease a range to be smoothed by the smoothing filter as the level of noise reduction is low and may increase the range to be smoothed by the smoothing filter as the level of noise reduction is high.

According to the invention, by performing a noise reduction process so that the level of noise reduction with respect to a radiological image is low as a mammary gland content ratio of the breast on a radiological image obtained by image-capturing the breast is high, and performing the noise reduction process so that the level of noise reduction with respect to the radiological image is high as the mammary gland content ratio is low, it is possible to reduce noise while leaving thin shading of mammary glands that appears on the radiological image obtained by image-capturing the breast.

DESCRIPTION OF THE PREFERRED EMBODIMENTS

Figure 1:
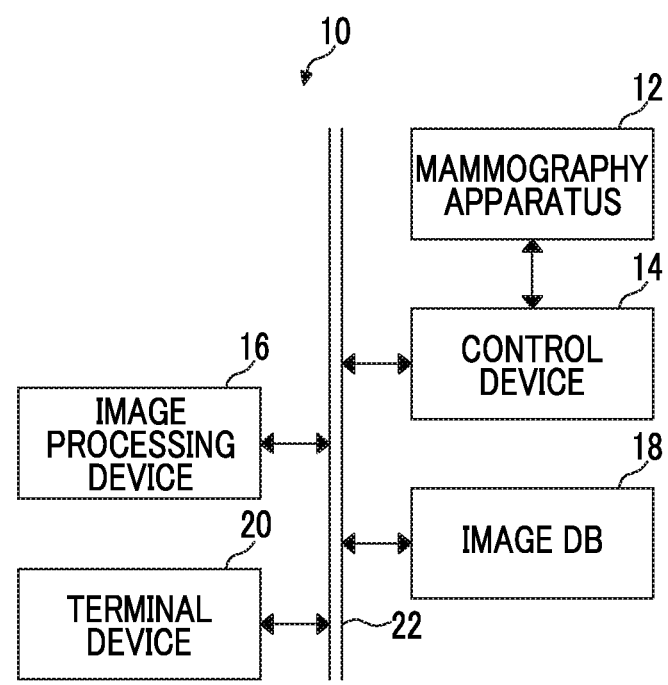
FIG. 1 is a schematic block diagram illustrating a configuration of a medical system to which a noise reduction device according to an embodiment of the invention is applied.

Hereinafter, embodiments of the invention will be described with reference to the accompanying drawings. FIG. 1 is a schematic block diagram illustrating a configuration of a medical system to which a noise reduction device according to a first embodiment of the invention is applied. As shown in FIG. 1, a system 10 includes a mammography apparatus 12 provided in a medical facility or the like, a control device 14 that controls the mammography apparatus 12, an image processing device 16 that performs image processing with respect to a breast image captured by the mammography apparatus 12, an image database 18 that stores the breast image, and a doctor's terminal device 20 that is provided with a high-definition monitor (not shown) for reading. These devices are connected to each other through a network 22.

Figure 2:
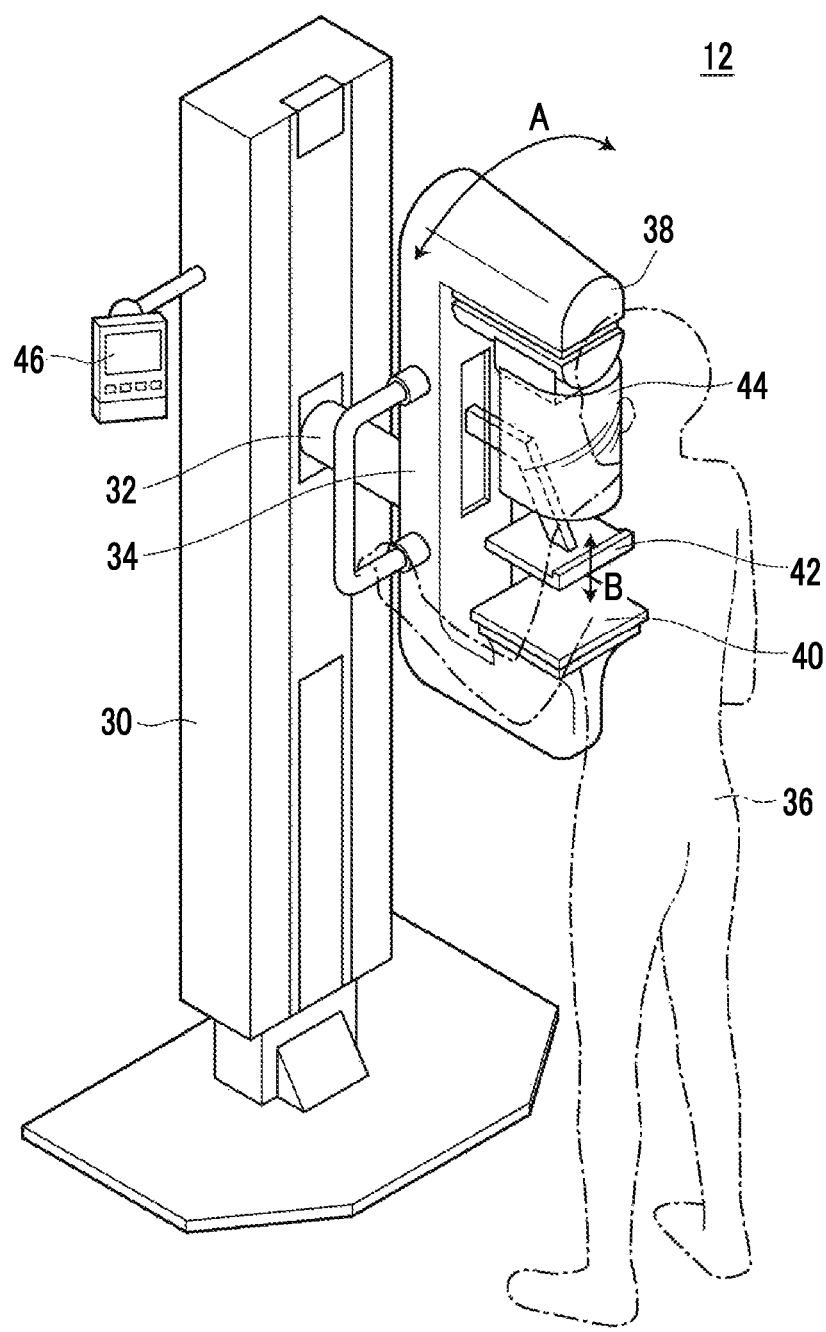
FIG. 2 is a schematic diagram illustrating a configuration of a mammography apparatus.

FIG. 2 is a schematic diagram illustrating a configuration of the mammography apparatus 12. As shown in FIG. 2, the mammography apparatus 12 includes a base 30 provided in a stand state; an arm portion 34 fixed to a rotation shaft 32 provided an approximately central portion of the base 30; an X-ray source storage section 38 that accommodates an X-ray source that irradiates the breast of a subject 36 with radiation (X-rays), and is fixed to an end portion of the arm portion 34; an image capturing stand 40 that accommodates a solid detector that detects the X-rays that passes through the breast to acquire a breast image which is a radiological image of the breast, and is fixed to the other end portion of the arm portion 34; and a compression plate 42 that compresses the breast with respect to the image capturing stand 40.

The arm portion 34 to which the X-ray source storage section 38, the image capturing stand 40, and the compression plate 42 are connected rotates in an arrow A direction shown in FIG. 2 centering around the rotation shaft 32 to adjust an image capturing direction with respect to the breast of the subject 36. The compression plate 42 is disposed between the X-ray source storage section 38 and the image capturing stand 40 in a state of being connected to the arm portion 34, and is configured to be displaced in an arrow B direction shown in FIG. 2.

In order to protect the vicinity of the face of the subject 36 from irradiation of the X-rays, a face guard sheet 44 formed of a member that shields the X-rays is provided in the X-ray source storage section 38. Further, a display 46 that displays image capturing information about an image capturing portion, an image capturing direction, and the like of the subject 36, ID information of the subject 36, and the like is provided to the base 30.

Figure 3:
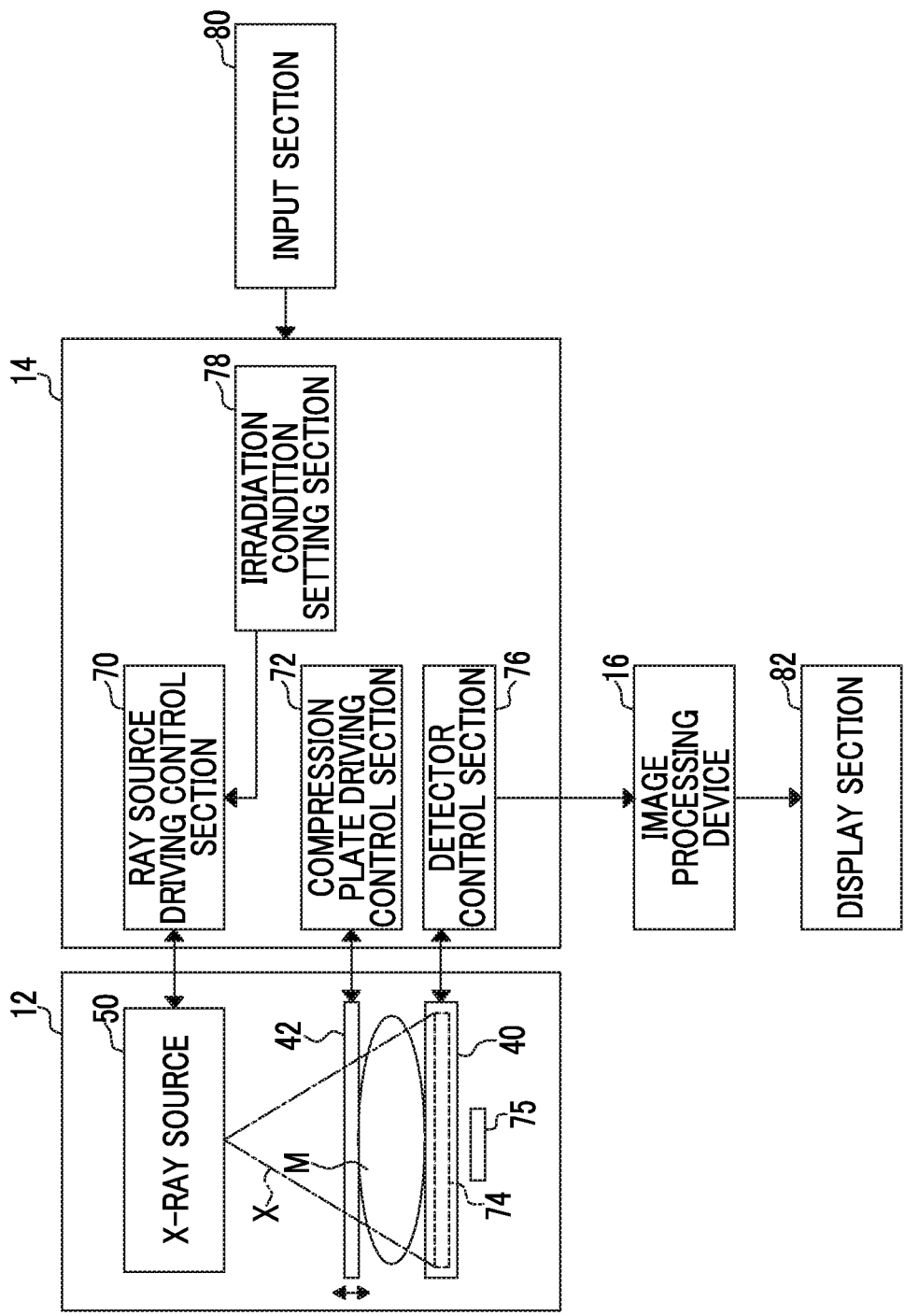
FIG. 3 is a block diagram of a control circuit that forms a mammography apparatus and a control device.

FIG. 3 is a block diagram of a control section that forms a mammography apparatus and a control device in the embodiment of the invention. The control device 14 that controls the mammography apparatus 12 includes a ray source driving control section 70 that driving-controls an X-ray source 50 according to a predetermined irradiation condition; a compression plate driving control section 72 that driving-controls the compression plate 42 and compresses the breast M of the subject 36 with respect to the image capturing stand 40; a detector control section 76 that controls a detector 74 accommodated in the image capturing stand 40 and acquires a radiological image; and an irradiation condition setting section 78 that sets irradiation conditions in image capturing. An input section 80 for performing a variety of input operations with respect to the control device 14 is connected to the control device 14. The input section 80 may employ a keyboard, and/or a mouse, and may further employ a touch panel, an operation panel, or the like.

The above-described irradiation conditions are conditions for adjusting an energy spectrum (radiation quality) of X-rays which are applied to the breast M to acquire a breast image having an appropriate contrast, and for example, may include the type of a target that forms the X-ray source 50, the type of a filter, a tube voltage applied between a filament and the target, and the dose of exposure. The dose of exposure is determined by the product of a tube current (mA) and an exposure time (sec).

The detector 74 can repeatedly perform recording and reading of a radiological image. The detector 74 may employ a so-called direct-type radiation detector that directly receives radiation to generate electrical charges, or may employ a so-called indirect-type radiation detector that first converts radiation into visible light and converts the visible light into an electric charge signal. Further, it is preferable that a so-called TFT reading method for switching on or off a thin film transistor (TFT) switch to read a radiological image signal or a so-called an optical reading method for applying reading light to read a radiological image signal is used as a method of reading a radiological image signal, but the invention is not limited thereto, and may employ other methods.

A radiation dose detector 75 is disposed under the detector 74, and for example, an automatic exposure control (AEC) sensor in which semiconductor detectors are arranged is used as a sensor that measures the dose of radiation. In order to acquire an appropriate image density (pixel value), the AEC sensor measures the dose of radiation that passes through the breast to determine an exposure time. Normally, the position of the breast is adjusted for image capturing so as to measure the dose of radiation exposed to approximately the center of the breast.

The image processing device 16 is a computer that performs image processing with respect to a radiological image obtained by image-capturing the breast, acquired by the mammography apparatus 12, and includes a known hardware configuration including a central processing unit (CPU), a main storage device, an auxiliary storage device, an input/output interface, a communication interface, an input device (a mouse, a keyboard, or the like), a display device (a display monitor), a data bus, and the like, in which a known operating system or the like is installed. The noise reduction process of the invention may be installed in the image processing device 16, and may be realized by executing an installed program from a recording medium such as a compact disc read only memory (CD-ROM) or the like. Further, the program may be installed by being downloaded from a storage device of a server connected through a network such as the Internet. In addition, a display 82 such as a liquid crystal display is connected to the image processing device 16. A processed radiological image is displayed on the display 82, so that the radiological image can be observed.

Figure 4:
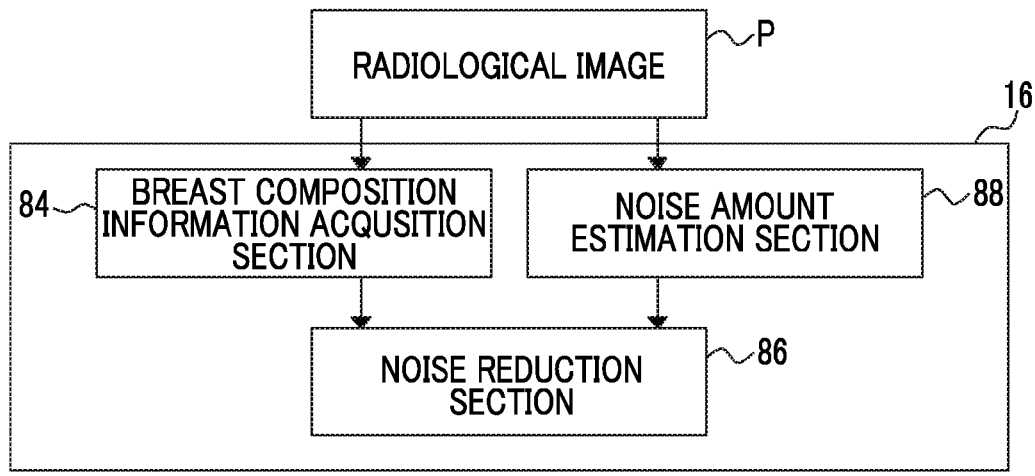
FIG. 4 is a block diagram of a noise reduction unit according to a first embodiment of the invention.

FIG. 4 is a block diagram illustrating a noise reduction unit of the image processing device 16 according to a first embodiment. As shown in the figure, the noise reduction unit in the embodiment of the invention includes a breast composition information acquisition section 84, a noise reduction section 86, and a noise amount estimation section 88.

The breast composition information acquisition section 84 acquires a mammary gland content ratio from a radiological image P acquired by applying radiation to the breast of a subject. The dose of radiation applied to the breast may be calculated from radiation conditions given to the ray source driving control section 70, and an attenuation factor of the dose of the applied radiation is changed between adipose tissue and mammary gland tissue in the breast. Accordingly, if the thickness of the breast can be known, it is possible to estimate the amounts of the adipose tissue and the mammary gland tissue from the dose of radiation applied to the breast and the dose of radiation that reaches each pixel. Thus, the position of the compression plate which is moved up and down by the compression plate driving control section 72 is acquired, the thickness of the breast is detected from the position of the compression plate, and an approximate ratio of the adipose tissue and the mammary gland tissue is obtained from a difference between the dose of radiation that reaches each pixel (that is, a pixel value of each pixel) and the dose of radiation that is applied to the breast to calculate the mammary gland content ratio for each pixel.

Alternatively, it is estimated that pixel values of pixels which are present at a predetermined distance from a skin line are obtained by image-capturing only a fat component. An auxiliary image may be generated using these pixel values under the assumption that the entire breast is configured by only fat using the pixel value, and then, pixel values of respective pixels of the auxiliary image and the radiological image P may be compared to calculate a mammary gland content ratio in each pixel. Specifically, for example, a method disclosed in JP2010-253245A may be used.

Further, using a configuration in which in order to perform the automatic exposure control using the AEC, a pre-captured image acquired by pre-irradiation performed before main image capturing is performed is analyzed, and thus, it is possible to determine a mammary gland content ratio by analyzing the pre-captured image obtained by the pre-image capturing. By performing the analysis of the pre-captured image to calculate the mammary gland content ratio of each pixel together with the main image capturing, it is possible to reduce the entire processing speed.

Figure 7:
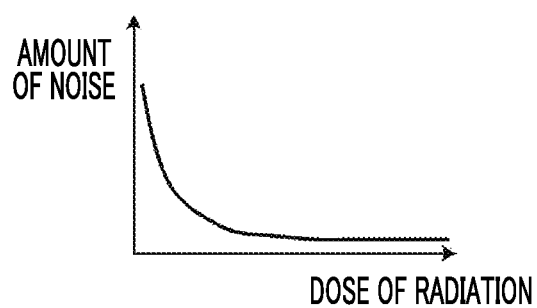
FIG. 7 is a diagram illustrating a relationship between the dose of radiation and the amount of noise.

The noise amount estimation section 88 estimates the amount of noise according to information indicating the dose of radiation that is applied to the breast and reaches the detector 74. Specifically, as the dose of radiation that reaches the detector 74, the amount of noise is calculated for each pixel, using the pixel values of the radiological image P obtained from the detector 74, based on a lookup table (LUT) of the amount of noise and the pixel values. The LUT is obtained in consideration of sensitivity or electric noise of the detector 74, and as shown in FIG. 7, an LUT in which the amount of noise increases as the dose of radiation decreases. For example, as disclosed in JP2005-021456A or JP4679710B, a noise amount estimating technique that estimates the amount of noise from an S value (reading sensitivity) and an L value (latitude) may be used. Specifically, by calculating backward the dose of radiation for each pixel from the S value and the L value, and the pixel value of each pixel, it is possible to estimate the amount of noise for each pixel based on the dose of radiation.

The noise reduction section 86 performs different noise reductions between a breast region on a high density breast image with a large amount of mammary glands and a breast region on a fatty breast image with a small amount of mammary glands. Since the high density breast image with the large amount of mammary glands has a small irregularity in the pixel values in the breast region and the fatty breast image with the small amount of mammary glands has a large irregularity in the pixel values, if the same noise control is performed with respect to the high density breast image and the fatty breast image, thin shading such as mammary glands becomes crushed in the high density breast image.

At a position of each pixel of the radiological image P, by checking which distribution pixel values of pixels in the vicinity of the pixel show, it is determined whether each pixel is present in a region having a large amount of mammary glands or in a region having a small amount of mammary glands, to thereby change the level of noise reduction.

Figure 6A:
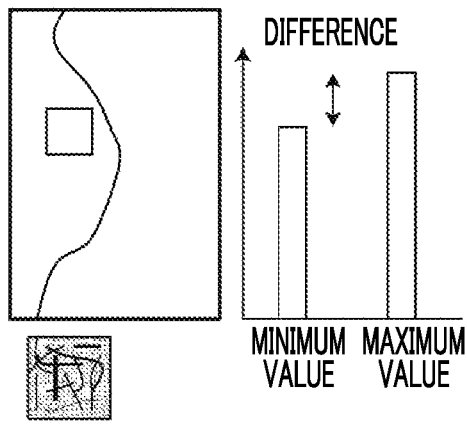
FIG. 6A and FIG. 6B are a diagram illustrating irregularities of pixel values of a breast region of a high density breast image and a breast region of a fatty breast image.
Figure 6B:
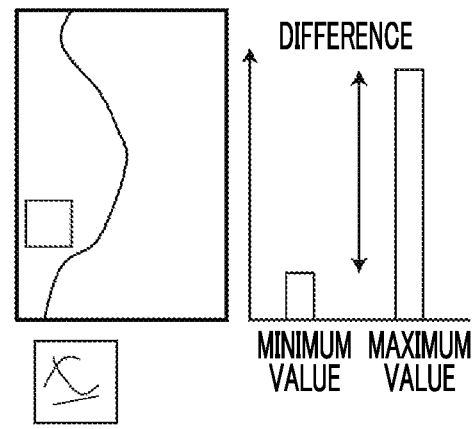

For example, using each pixel as an attention pixel, in a case where a rectangular region of a predetermined size centering around the attention pixel is set as an interest region, as shown in FIG. 6A and FIG. 6B, in the breast region of the high density breast image, a variance of pixel values of pixels in the interest region is small, and a difference between a maximum value and a minimum value of the pixel values of the pixels in the interest region is small (FIG. 6A). On the other hand, in the breast region of the fatty breast image, a variance of pixel values of pixels in the interest region is large, and a difference between a maximum value and a minimum value of the pixel values of the pixels in the interest region is large (FIG. 6B). Thus, the noise reduction section 86 calculates the level of smoothing in noise reduction (noise reduction target value) to correspond to the size of a change of the mammary gland content ratio of the pixels in the interest region. The interest region is not limited to the rectangular shape, and may be a circular shape or other shapes. Further, the size of the interest region may be appropriately determined according to the size and resolution of the radiological image P.

Since noise is included in the interest region, or since a structure other than the mammary gland, such as a skin line, is included therein, a difference between a maximum value and a minimum value of actual pixel values in the interest region is easily affected by information about the noise or structure. By estimating a distribution range of pixel values based on mammary glands and fat in the interest region to determine the level of noise reduction, it is possible to perform noise reduction while leaving thin shading with a small density difference, such as mammary glands. The distribution of pixel values in which the influence of the noise or the structure other than the mammary glands is removed, as shown in FIG. 6A and FIG. 6B, is close to the distribution of the mammary gland content ratio. Thus, an index value indicating the size of the change of the mammary gland content ratio of the pixels that are present in the interest region is acquired from the mammary gland content ratio of the pixels that are present in the interest region as an index value corresponding to the level of smoothing of noise reduction. Hereinafter, it is assumed that the index value and a target value of noise reduction are the same value.

For example, in a portion where a large amount of mammary glands are present, a median value of the mammary gland content ratio of the pixels in the interest region is large and the level of smoothing of noise reduction is low, but in a portion where a small amount of mammary glands are present, a median value of the mammary gland content ratio of the pixels in the interest region is small and the level of smoothing of noise reduction is high. Thus, for example, the level of smoothing of noise reduction may be calculated using the following Expression (1).

$$\text{Level of smoothing (target value)} = \alpha/\text{median value of mammary gland content ratio in interest region} \quad (1)$$

Here, $\alpha$ is a positive constant value.

When calculating the level of smoothing, the median value in Expression (1) may be an average value of pixel values in the interest region, a modal value, or the like.

Alternatively, as the level of smoothing, a difference between a maximum value and a minimum value of the mammary gland content ratio in the interest region, a variance of the mammary gland content ratios in the interest region, or the like may be used.

If the target value of noise reduction is small, the level of noise reduction of the attention pixel is set to be small, and if the target value of noise reduction is large, the level of noise reduction of the attention pixel is set to be high. Specifically, for example, it is possible to decrease the level of noise reduction by narrowing a range of a smoothing filter, and to increase the level of noise reduction by enlarging the range of the smoothing filter.

Further, by calculating a direction component from a peripheral structure of each pixel using an edge detection filter or the like at a position of each pixel and performing filtering along the direction, it is possible to reduce noise while storing an edge. For example, using a technique disclosed in JP4679710B, it is possible to determine whether each pixel is present on an edge from a direction component of a density gradient of pixels in the vicinity of a position of each pixel, and when each pixel is present on the edge, it is possible to use a smoothing filter that performs smoothing while leaving a component in an edge direction.

In addition, in the case where the target value of noise reduction is small, a probability that thin shading with a small concentration difference occurs is high. Accordingly, in the case where the target value of noise reduction is small, a region for calculating a direction component that appears in the pixels in the vicinity of the position of each pixel is set to be large, and thus, it is possible to detect a large edge. Specifically, a filter size of the edge detection filter is set to be large. According to the direction and size of the detected edge, a smoothing direction in the smoothing filter and a characteristic of the smoothing filter are determined. Thus, it is possible to perform smoothing while leaving a thin and large mammary gland structure with a small concentration difference in the interest region.

Further, a smoothing range in the smoothing filter is changed so that the level of noise reduction is high as the amount of noise estimated by the noise amount estimation section 88 is large and is low as the estimated amount of noise is small. Here, the amount of noise includes quantum noise and electric noise.

The noise reduction section 86 determines the level of noise reduction from the amount of noise and the target value estimated by the noise amount estimation section 88. Specifically, with respect to the level of noise reduction, a two-dimensional LUT selected as a combination of the target value and the amount of noise is prepared in advance, and a noise reduction level indicating the level of noise reduction is calculated using the LUT. The two-dimensional LUT is determined so that the level of noise reduction is obtained from the "amount of noise" and the "target value". The relationship between the level of noise reduction and the LUT is shown in the following Expression (2). The noise reduction section 86 selects a smoothing filter having a size corresponding to the level of noise reduction obtained by the LUT.

$$\text{Level of noise reduction} = \text{LUT (amount of noise, and target value)} \quad (2)$$

Specifically, the filter size for noise reduction selected by the amount of noise and the target value is shown as in the following Table 1.

TABLE 1

| | Target value large | Target value small |
|---|---|---|
| The amount of noise Large | Filter large 7 × 7 (pixels) | Filter small 3 × 3 (pixels) |
| The amount of noise small | Filter medium 5 × 5 (pixels) | Filter small 3 × 3 (pixels) |

Since the filter sizes in Table 1 are exemplary, and a limit level of noise reduction where mammary glands that appear as thin shading are not deleted can be known according to the target value, it is possible to determine the filter size according to empirical values. In Table 1, for ease of description, an example of the filter size determined only by the size of the target value and the amount of noise is shown, but it is preferable to prepare an LUT in which plural numerical value ranges of the target value and plural numerical value ranges of the amount of noise are combined and to perform noise reduction according to fine conditions.

Figure 5:
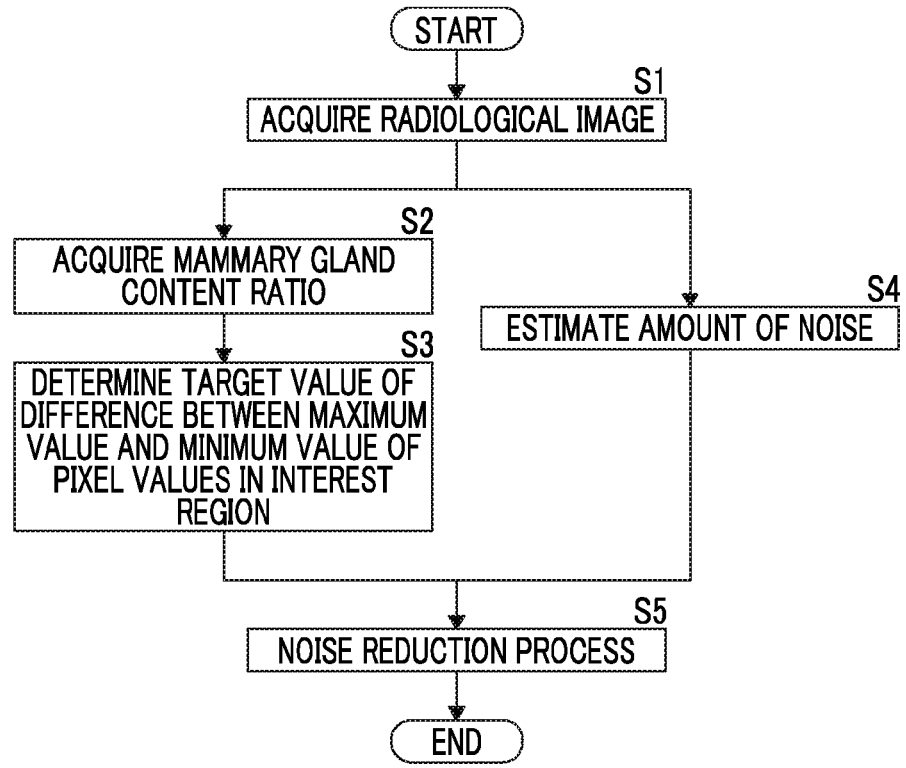
FIG. 5 is a flowchart illustrating a processing flow of a medical system and an operation of an image processing device, according to the first embodiment of the invention.

Next, a processing flow of a medical system and an operation of an image processing device, according to the first embodiment of the invention, will be described with reference to a flowchart of FIG. 5.

An engineer positions the breast M with respect to the image capturing stand 40 of the mammography apparatus 12, and then, moves the compression plate 42 by the compression plate driving control section 72 to compress the breast M. When the breast M is compressed in a desired state, the movement of the compression plate 42 is stopped. Then, if an image capturing switch (not shown) is turned on by the engineer, the ray source driving control section 70 applies X-rays to the breast M according to irradiation conditions set by the irradiation condition setting section 78 to perform image capturing (S1).

A breast image which is the radiological image P of the breast M recorded on the detector 74 is read by the detector control section 76 through the image capturing, and is supplied to the image processing device 16. In the image processing device 16, the breast composition information acquisition section 84 acquires a mammary gland content ratio of each pixel from the radiological image P obtained by applying the radiation to the breast of a subject (S2).

The noise reduction section 86 sets an interest region using each pixel as an attention pixel, calculates mammary gland content ratios in the interest region, calculates a median value of the mammary gland content ratios in the interest region, and determines a target value of noise reduction for each pixel (attention pixel) according to Expression (1) (S3). Further, the noise amount estimation section 88 estimates the amount of noise for each pixel (S4).

The noise reduction section 86 acquires the level of noise reduction using an LUT based on the target value of noise reduction of each pixel and the amount of noise estimated by the noise amount estimation section 88, and determines the size of a smoothing filter based on the obtained level of noise reduction. Further, the noise reduction section 86 calculates a direction component from a peripheral structure of each pixel using an edge detection filter or the like at a position of each pixel, and uses a smoothing filter capable of performing filtering along the direction. A smoothing process is performed for each pixel using the smoothing filter determined as described above (S5).

The above-described processes in S3 to S5 are performed with respect to all pixels excluding pixels in a region to which the radiation is directly applied on the radiological image P of the breast M while scanning pixels of the radiological image P.

As described above, in the first embodiment, by determining, for each pixel, the level of noise reduction from the mammary gland content ratio of pixels in the vicinity of each pixel and performing noise reduction, it is possible to reduce noise while leaving thin shading such as mammary glands.

Further, in the above-described first embodiment, a configuration in which the level of noise reduction is determined, for each pixel, based on the mammary gland content ratios of pixels in the vicinity of each pixel and the amount of noise for each pixel is shown, but a configuration in which the level of noise reduction is determined on the assumption that the amount of noise is approximately constant over the entire image may be used.

Next, a medical system to which a noise reduction device according to a second embodiment is applied will be described. Since an overall configuration of the medical system is the same as in the first embodiment in FIG. 1, description thereof will not be repeated.

Figure 8:
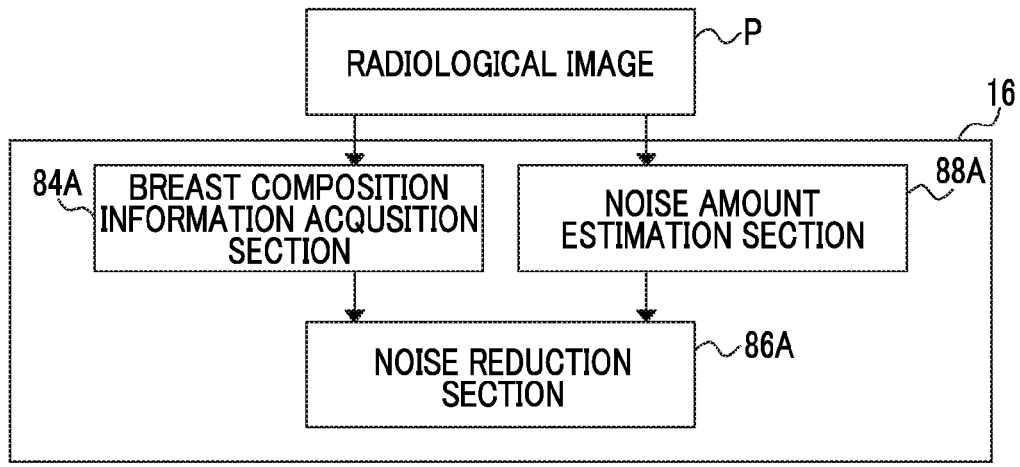
FIG. 8 is a block diagram of a noise reduction unit according to a second embodiment of the invention.

FIG. 8 is a block diagram illustrating a noise reduction unit of the image processing device 16 according to the second embodiment. As shown in the figure, the noise reduction unit in this embodiment of the invention includes a breast composition information acquisition section 84A, a noise reduction section 86A, and a noise amount estimation section 88A. In this embodiment, instead of a configuration in which the mammary gland content ratio and the amount of noise are acquired for each pixel and the level of noise reduction is changed in the unit of a pixel, described in the first embodiment, a configuration in which the mammary gland content ratio and the amount of noise are acquired from the entirety of the radiological image P and approximately the same level of noise reduction is performed for the entire image is used.

The breast composition information acquisition section 84A calculates a mammary gland content ratio from the area of a breast region and the area of a mammary gland region on the radiological image P. A region excluding a region to which radiation is directly applied, on the radiological image P, is acquired as the breast region. With respect to a mammary gland region, binary processing is performed with respect to the breast region on the radiological image P using a threshold value for dividing a pixel value in a region considered as mammary glands and a pixel value in a region considered as fat to acquire a binary image, and a portion having a pixel value equal to or greater than the threshold value in the binary image is acquired as the mammary gland region. Thus, the ratio of the area of the mammary gland region to the area of the breast region is acquired as the mammary gland content ratio.

The noise amount estimation section 88A acquires the dose of radiation detected by an AEC sensor as information indicating the dose of radiation that reaches the detector 74. Alternatively, in a case where the detector is an optical reading detector that reads a radiological image by application of reading light, a reading sensitivity may be acquired as information indicating the dose of radiation that reaches the detector 74.

The noise reduction section 86A determines the level of noise reduction from the mammary gland content ratio acquired by the breast composition information acquisition section 84A and the amount of noise estimated by the noise amount estimation section 88A, and determines the size of a smoothing filter for smoothing a range corresponding to the level of noise reduction. Specifically, according to the mammary gland content ratio and the amount of noise, the level of noise reduction is stored in a two-dimensional LUT or the like. Further, it is determined whether each pixel is present on an edge using an edge detection filter, and filtering is performed along an edge direction, to thereby perform noise reduction using a smoothing filter that performs smoothing while maintaining the edge.

Figure 9:
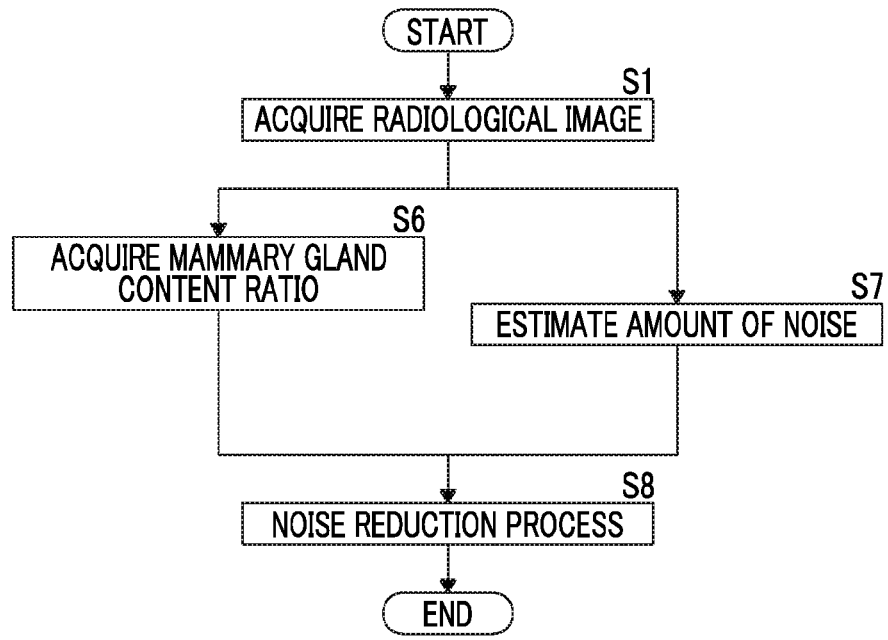
FIG. 9 is a flowchart illustrating a processing flow of a medical system and an operation of an image processing device, according to a second embodiment of the invention.

A processing flow of the medical system and an operation of the image processing device according to the second embodiment will be described with reference to a flowchart of FIG. 9.

In step S1, a radiological image P is acquired by image-capturing the breast M in a similar way to step S of the first embodiment.

Then, the breast composition information acquisition section 84A performs binary processing with respect to a breast region on the radiological image P to acquire a binary image, acquires the area of a mammary gland region, and acquires a ratio of the area of the mammary gland region to the area of the breast region as a mammary gland content ratio of the entire radiological image P (S6). Further, the noise amount estimation section 88A acquires the amount of noise of the entire radiological image P (S7). The noise reduction section 86A determines the size of a smoothing filter based on the mammary gland content ratio and the amount of noise, determines a direction of an edge in each pixel using an edge detection filter, and performs a noise reduction process using the smoothing filter for performing smoothing while maintaining the edge at a position of each pixel (S8).

As described above, in the second embodiment, while the level of noise reduction is constantly maintained in the entire radiological image, since the level of noise reduction is determined according to the mammary gland content ratio, it is possible to perform smoothing while leaving a thin structure such as mammary glands.

In the first embodiment, the amount of noise is estimated for each pixel, but instead of the estimation of the amount of noise in the first embodiment, the amount of noise estimated by the noise amount estimation section 88A in the second embodiment may be used, so that the level of noise reduction can be determined on the assumption that a constant ratio of noise is present over the entire pixels of the radiological image.

Further, in the first embodiment, the mammary gland content ratio and the amount of noise are estimated for each pixel, but for example, using two pixels or four pixels that are adjacent to each other as a unit pixel, the mammary gland content ratio and the amount of noise may be estimated for each unit pixel. Alternatively, a group of plural pixels that are close to each other may be set as a unit pixel.

Further, in the first and second embodiments, the noise reduction process is performed using a radiological image obtained in the system that captures the radiological image of a subject using the radiation detector, but in a case where radiological image information of a subject is stored and recorded on a storage phosphor sheet which is a radiation detector disclosed in JP 1996-266529A (JP-H08-266529A), JP 1997-22039A (JP-H09-22039A), or the like, and a radiological image is acquired by being optically read from the storage phosphor sheet, similarly, the invention can be applied.

Further, in the first and second embodiments, while it is natural to apply the noise reduction described in the embodiments with respect to a breast region, noise reduction in a region other than the breast region may be the noise reduction described in the embodiments, or may be noise reduction determined by other methods.

What is claimed is:

1. A noise reduction device comprising:
   at least one processor configured to operate as:
   a breast composition information acquisition section that irradiates a breast of a subject with radiation and acquires a mammary gland content ratio in each unit pixel including a predetermined number of pixels that form a breast region of a radiological image obtained by the radiation that passes through the breast; and
   a noise reduction section that sets, using each unit pixel as an attention pixel, an interest region including the attention pixel, acquires an index value indicating a size of a change of the mammary gland content ratio of each unit pixel that is present in the interest region from the mammary gland content ratios of the plurality of unit pixels that is present in the interest region, performs a noise reduction process so that the level of noise reduction at a position of the attention pixel is low as the index value is small, and performs the noise reduction process so that the level of noise reduction at the position of the attention pixel is high as the index value is large.

2. The noise reduction device according to claim 1, wherein the noise reduction section calculates the index value so that the index value is small as a representative value of the mammary gland content ratios of the plurality of unit pixels that is present in the interest region is large, and is large as the representative value of the mammary gland content ratios is small.

3. The noise reduction device according to claim 1, wherein the breast composition information acquisition section acquires the mammary gland content ratio in each unit pixel according to the dose of the radiation applied to the breast, a pixel value of each unit pixel of the radiological image, and a thickness of the breast.

4. The noise reduction device according to claim 2, wherein the breast composition information acquisition section acquires the mammary gland content ratio in each unit pixel according to the dose of the radiation applied to the breast, a pixel value of each unit pixel of the radiological image, and a thickness of the breast.

5. The noise reduction device according to claim 1, wherein the breast composition information acquisition section acquires the mammary gland content ratio in each unit pixel using a pixel value of a location which is estimated to be formed by only adipose tissue in the breast region of the radiological image and a pixel value of each unit pixel in the breast region.

6. The noise reduction device according to claim 2, wherein the breast composition information acquisition section acquires the mammary gland content ratio in each unit pixel using a pixel value of a location which is estimated to be formed by only adipose tissue in the breast region of the radiological image and a pixel value of each unit pixel in the breast region.

7. The noise reduction device according to claim 1, wherein the unit pixel is a single pixel.

8. The noise reduction device according to claim 2, wherein the unit pixel is a single pixel.

9. The noise reduction device according to claim 3, wherein the unit pixel is a single pixel.

10. The noise reduction device according to claim 4, wherein the unit pixel is a single pixel.

11. The noise reduction device according to claim 5, wherein the unit pixel is a single pixel.

12. The noise reduction device according to claim 6, wherein the unit pixel is a single pixel.

13. A noise reduction device comprising:
    at least one processor configured to operate as:
    a breast composition information acquisition section that irradiates a breast of a subject with radiation and acquires a mammary gland content ratio at which mammary glands are included in the breast from a radiological image obtained by the radiation that passes through the breast; and
    a noise reduction section that performs a noise reduction process so that the level of noise reduction with respect to the radiological image is low as the mammary gland content ratio is high, and performs the noise reduction process so that the level of noise reduction with respect to the radiological image is high as the mammary gland content ratio is low.

14. The noise reduction device according to claim 13, wherein the breast composition information acquisition section calculates the mammary gland content ratio from a ratio between the area of a breast region on the radiological image and the area of a mammary gland region on the radiological image.

15. The noise reduction device according to claim 1, further comprising:
    a noise amount estimation section that estimates the amount of noise according to information indicating the dose of radiation which is applied to the breast and reaches the radiological image, wherein the noise reduction section increases the level of noise reduction as the estimated amount of noise is large, and decreases the level of noise reduction as the estimated amount of noise is small.

16. The noise reduction device according to claim 1, wherein the noise reduction section performs the noise reduction process using a smoothing filter, and decreases a range to be smoothed by the smoothing filter as the level of noise reduction is low, and increases the range to be smoothed by the smoothing filter as the level of noise reduction is high.

17. A noise reduction method in the noise reduction device according to claim 1 including a breast composition information acquisition section and a noise reduction section, the method comprising:

a breast composition information acquisition step of irradiating a breast of a subject with radiation and acquiring a mammary gland content ratio in each unit pixel including a predetermined number of pixels that form a breast region of a radiological image obtained by the radiation that passes through the breast, by the breast composition information acquisition section; and a noise reduction step of setting, using each unit pixel as an attention pixel, an interest region including the attention pixel, acquiring an index value indicating a size of a change of the mammary gland content ratio of each unit pixel that is present in the interest region from the mammary gland content ratios of the plurality of unit pixels that is present in the interest region, performing a noise reduction process so that the level of noise reduction at a position of the attention pixel is low as the index value is small, and performing the noise reduction process so that the level of noise reduction at the position of the attention pixel is high as the index value is large, by the noise reduction section.

18. A non-transitory computer readable recording medium storing a noise reduction program that causes a computer to function as:

a breast composition information acquisition section that irradiates a breast of a subject with radiation and acquires a mammary gland content ratio in each unit pixel including a predetermined number of pixels that form a breast region of a radiological image obtained by the radiation that passes through the breast; and a noise reduction section that sets, using each unit pixel as an attention pixel, an interest region including the attention pixel, acquires an index value indicating a size of a change of the mammary gland content ratio of each unit pixel that is present in the interest region from the mammary gland content ratios of the plurality of unit pixels that is present in the interest region, performs a noise reduction process so that the level of noise reduction at a position of the attention pixel is low as the index value is small, and performs the noise reduction process so that the level of noise reduction at the position of the attention pixel is high as the index value is large.

19. A noise reduction method in the noise reduction device according to claim 1 including a breast composition information acquisition section and a noise reduction section, the method comprising:

using at least one processor to perform steps of:

a breast composition information acquisition step of irradiating a breast of a subject with radiation and acquiring a mammary gland content ratio at which mammary glands are included in the breast from a radiological image obtained by the radiation that passes through the breast, by the breast composition information acquisition section; and a noise reduction step of performing a noise reduction process so that the level of noise reduction with respect to the radiological image is low as the mammary gland content ratio is high, and performing the noise reduction process so that the level of noise reduction with respect to the radiological image is high as the mammary gland content ratio is low, by the noise reduction section.

20. A non-transitory computer readable recording medium storing a noise reduction program that causes a computer to function as:

a breast composition information acquisition section that irradiates a breast of a subject with radiation and acquires a mammary gland content ratio at which mammary glands are included in the breast from a radiological image obtained by the radiation that passes through the breast; and a noise reduction section that performs a noise reduction process so that the level of noise reduction with respect to the radiological image is low as the mammary gland content ratio is high, and performs the noise reduction process so that the level of noise reduction with respect to the radiological image is high as the mammary gland content ratio is low.

* * * * *